United States Patent [19]
Obagi et al.

[11] Patent Number: 5,166,176

[45] Date of Patent: * Nov. 24, 1992

[54] COMPOSITION FOR HEALING DAMAGED SKIN

[76] Inventors: Zein E. Obagi, 200 Surrey Dr., Bonita, Calif. 92002; George H. Michel, 343 Oak Knoll Dr., Glendora, Calif. 91740

[*] Notice: The portion of the term of this patent subsequent to Oct. 17, 2006 has been disclaimed.

[21] Appl. No.: 328,284

[22] Filed: Mar. 24, 1989

Related U.S. Application Data

[63] Continuation-in-part of Ser. No. 947,085, Dec. 29, 1986, Pat. No. 4,874,361.

[51] Int. Cl.$^5$ ............................................. A61K 31/19
[52] U.S. Cl. ..................... 514/557; 514/731
[58] Field of Search ................. 514/557, 731

[56] References Cited

U.S. PATENT DOCUMENTS

| | | | |
|---|---|---|---|
| 3,973,001 | 8/1976 | Jaeger et al. | 424/101 |
| 4,072,639 | 2/1978 | Yamaguchi et al. | 430/531 |
| 4,202,323 | 5/1980 | Zweig et al. | 128/1.1 |
| 4,235,889 | 11/1980 | Evers | 424/195 |
| 4,424,234 | 1/1984 | Alderson et al. | 424/317 |
| 4,558,700 | 12/1985 | Mutzhas | 128/395 |

OTHER PUBLICATIONS

R. J. McIlroy, *The Plant Glycosides*, 1951, Ch. IX.
Y. Birk and I. Peri, "Saponins", Ch. 6 of *Toxic Constituents of Plant Foodstuffs*, I. Liener (ed.), 1980.
Noller, *Chemistry of Organic Compounds*, (3rd. ed., 1965), Ch. 42.
Gennaro, *Remington's Pharmaceutical Sciences*, Ch. 25 (17th Ed., 1985).
*Ullman's Encyclopedia of Technical Chemistry*, vol. 8, (4th ed., 1972).
*Ullman's Encyclopedia of Technical Chemistry*, vol. 11, (3rd ed., 1960), pp. 440-461.
Chemical Abstracts 100:179960w (1984).
Chemical Abstracts 101:116595f (1984).
The Merck Manual, 10th Ed., 1961, pp. 1444-1446.

*Primary Examiner*—Leonard Schenkman
*Attorney, Agent, or Firm*—Brown, Martin, Haller & McClain

[57] ABSTRACT

A composition is described for treating human skin of all races for a wide variety of skin ailments, including acne, blemishing, aging, sun damage, cancerous lesions and other problems associated with skin disorders. The composition comprises trichloroacetic acid, a surfactant having cell growth stimulatory properties and a humectant-emollient. The ratio of the ingredients can be varied to effect optimal treatment for a particular type of skin. The composition is used by being applied topically to the damaged skin region. Several days following treatment, the damaged area peels off, and a new layer of vibrant, evenly colored, healthy skin is apparent.

22 Claims, No Drawings

COMPOSITION FOR HEALING DAMAGED SKIN

CROSS-REFERENCE TO RELATED APPLICATION

This application is a continuation-in-part of application Ser. No. 06/947,085, filed Dec. 29, 1986, now U.S. Pat. No. 4,874,361.

BACKGROUND OF THE INVENTION

Over the years, a variety of compositions have been developed to treat chronic skin problems such as acne, sun damage, precancerous lesions, scars, pigmentation disorders, wrinkles and the like. These either supplement or prevent the loss of nutrients needed for healthy skin or remove regions of damaged skin. Included in the former category are skin creams, lotions and ointments that are generally available over-the-counter. These creams either act to prevent water loss from the skin or to deliver nutrients into the dermal layers. Suitable examples of such creams can be found in U.S. Pat. Nos. 4,424,234 and 4,235,889. Also, prescription medical creams and antibiotics used to treat acne vulgaris or other skin conditions are known to those skilled in the art.

For the most part, only three methods are now in routine medical use for removing damaged skin. They all involve the application of particular chemicals. The first can be termed the trichloroacetic acid peel; the second, the resorcinol or salicylic acid peel; and third, the chemical peel. All three are of only limited use.

The trichloroacetic acid peel involves the application of trichloroacetic acid to the damaged area, followed by a short reaction time to allow it to interact with the damaged skin. Several days later, the damaged area peels off. The limitation of this method in that it is generally not effective for dark skinned people with significant pigmentation because it peels the skin unevenly, and thus leaves unevenly pigmented skin. For that reason, only fair skinned people are peeled with trichloroacetic acid treatment. Blacks and other dark skin groups are excluded.

The second peal process involves the use of either resorcinol or salicylic acid. The use of either of these chemicals is generally restricted to correcting superficial skin problems. They are further limited in that they often can cause skin irritation.

The third peel process, or chemical peel, also has numerous drawbacks. First, it involves the use of phenol, which presents problems of toxicity in some cases. Thus, this method must be carried out in a hospital or in a similar controlled setting. In addition, the method is very painful and often requires that the patient be given medication during its application. Further, while the procedure does peel the skin evenly, it nevertheless often leaves uneven pigmentation of varying skin shades, or total loss of color. Finally, it does not lend itself to repeat applications because of its severe nature.

In addition to the above-described three types of skin peels, there exist a number of less useful materials and procedures. For example, short exposure to ultraviolet light (UVA or UVB wavelengths) is known to be beneficial for psoriasis, vitiligo and mycosis fungoids and simultaneously causes tanning of the skin. None of these methods uses full spectrum sun lamps.

It should be apparent from the above that there is a need for a composition for treating chronic skin disorders, particularly one which would be universally applicable to all races, that is easy to use and, if need be, can be used repeatedly.

SUMMARY OF THE INVENTION

The compositions of this invention are useful treating a wide variety of chronic skin problems, particularly pigmentation disorders, acne, wrinkles, aging spots and superficial precancerous skin spots. The compositions can be used alone, or with brief exposure to a suitable light source. They do not have undesirable long-term side effects, can be used on dark and light skins and can be reapplied for repeated treatments in particularly severe cases.

The compositions useful for treating distressed skin comprise trichloroacetic acid or an acid having equivalent therapeutic and toxicity properties, a surfactant having cell growth stimulatory properties and a humectant-emollient that enhances even application of the composition to the skin. In addition, anti-microbial agents or chemicals that prevent oxidation can be added to the composition. An important consideration in the present invention is that all of the components are appropriately non-toxic when used as defined herein, which distinguishes them markedly from many prior art materials such as phenol, which produce adverse effects on organs such as heart and liver.

The compositions are used by being applied topically to the damaged skin area. Depending on the type of skin disorder, as well as the race of the patient, the concentrations of the three main ingredients will vary. For light-skinned patients or for superficial skin problems, low concentrations of trichloroacetic acid will be utilized (about 10%), while for dark-skinned patients or if more severe treatment is required, concentrations up to approximately 50% will be employed. (All percentage concentrations herein are percentages by weight per unit volume unless otherwise noted.)

For treatment of deep skin disorders the effect of the composition is enhanced if a short time after application of the composition, the skin is irradiated with a light source that generates ultraviolet, infrared and full spectrum visible light. The light coacts with the composition thereby causing skin regeneration without tanning. Depending again on the severity of the skin disorder, exposure to the light source will be for either short or long durations of time. The latter generally will not exceed 15 minutes.

About three days following application of the composition, the skin begins to peel, and the peeling process is essentially complete by the end of the tenth day. The compositions can be used to treat virtually all parts of body skin and are not restricted to treatment of the face. Moreover, unlike many other compositions, the compositions described herein can be used repeatedly as often as is needed, as they do not irreversibly kill skin cells needed for future skin growth.

DETAILED DESCRIPTION OF THE INVENTION

The compositions of the invention comprises three critical components. The first is trichloroacetic acid or an acidic substance having equivalent therapeutic efficacy. The second is a surfactant having cell growth stimulatory activity, and the third is a humectant-emollient.

A variety of acidic substances may be useful in the composition, such as resorcinol or like materials which have therapeutic efficacies equivalent to that of trichloroacetic acid. Such materials will be known to those skilled in dermatological medicine. Preferred is trichloroacetic acid ($CCl_3COOH$) itself as it has been extensively tested in prior art peeling processes and found to be relatively safe for such treatments Generally, the composition will contain from 10 to about 50% trichloroacetic acid. Determinative of the concentration is whether a patient needs a superficial or deep peel, as well as the patient's skin color. For superficial treatments, a concentration of about 10% will generally be adequate, while for more severe cases, higher concentrations of trichloroacetic acid are desirable. It will usually be apparent to the physician what the preferred concentration of trichloroacetic acid is for a particular application. For those treatments where the concentration of trichloroacetic acid is in doubt, however, patch testing a very small area of the patient's skin will indicate the concentration of trichloroacetic acid that should be employed.

The use of trichloroacetic acid by itself or with an inert carrier is not novel, having been practiced for some time. However, as noted above, it has heretofore not been usable for other than fair-skinned patients because it causes uneven peeling and results in a blotchy effect on darker skins. Also, used alone it is a strong irritant to the skin, causing significant inflammation It is the discovery of this invention that the synergistic combination of an acid such as trichloroacetic acid with two additional components will produce a composition that provides even peeling and uniform treatment of skins of all shades and which does not irritate or inflame the skin.

The second component of the composition herein is a surfactant to reduce surface tension, ameliorate the tendency of the acid to cause skin irritation and inflammation and aid cell growth stimulatory activity. The general properties of surfactants are well known, and in the present invention the surfactant component acts in part to cause the acidic component to be evenly and thoroughly distributed across the treated area of skin and to penetrate uniformly into the dermal layers. The surfactant which are of use in the present invention are those which also have, in addition to their surfactant properties, cell growth stimulatory activity. There are a number of such surfactants, of both plant and animal origin Typical examples are epidermal growth factor and fibroblast growth factor. More preferred, however, in the present invention are the saponins, particularly the steroid saponins. The saponins are a well known class of glycosides which are widely distributed in plants. They are commonly divided into two subclasses, the triterpenoid saponins, which are based on a pentacyclic triterpene structure, and the steroid saponins which are based on a steroid nucleus. The saponins are well described in McIlroy, *The Plant Glycosides*, Chapter IX, (1951) and Noller, *Chemistry of Organic Compounds*, Chapter 42 (3rd Edn., 1965). Among the steroidal saponins are sarsapogenin and numerous similar compounds, usually containing additional hydroxyl and/or keto groups and/or double bonds, such as diosgenin, tigogenin and yuccagenin. Since these are naturally occurring materials, they are not necessarily isolated into individual compounds for use in the present composition. Rather the individual compounds or various mixtures thereof will be suitable in the present invention, since for the purposes of this invention the saponins, particularly the steroid saponins, essentially all possess the necessary surfactant/growth stimulation properties. It is also possible that in some applications the saponins may be used in the form of the plant sources without direct isolation of the saponin component.

The surfactant, preferably a saponin, will be present in the composition in a concentration of from about 0.01% to 2.0%. The exact concentration will depend on the depth of peel which is desired and on the particular surfactant used. If a greater depth of peel is desired more of the surfactant should be present. On the other hand, surfactants are known to have varying degrees of toxicity and that must be considered in determining whether a single deep peel is advisable or two or more peels of lesser depth, the latter serving to lessen the amount of surfactant received by the patient at any one time. Toxicity of the saponins is discussed in McIlroy, supra. and Gennaro, *Remington's Pharmaceutical Sciences*, Chapter 25 (17th ed., 1985). The present compositions are such, however, that the physician will have no difficulty determining the proper amount of surfactant to be used to produce the depth of peel appropriate to the patient.

Of particular use is a steroid saponin composition known as "Complex 272" commercially available from the Mikuda Company, which has been approved for use by the U.S. Food and Drug Administration under Registration No. 121.1163.

Several properties of the cell growth stimulatory ingredient merit discussion. In addition to stimulating dermal cell growth, a further desirable property is its capacity to penetrate into the skin, thereby stimulating cell growth in the layers beneath those that are being removed during the peel process. While steroid saponins have been determined to have this skin penetrating property, and therefore are the preferred embodiment in the instant invention, a variety of other cell growth stimulatory molecules can be combined with suitable skin penetrating agents, for example such as dimethyl sulfoxide, and hence be similarly employed. In addition, it is to be further anticipated that similar results can be realized by associating, via chemical coupling, sealing in lipid vesicles or other means, a surface active substance and a cell growth stimulatory compound. In this instance, the surface active property of the ingredient will not be intrinsic to the cell growth stimulatory property, but still be deliverable to the dermal layers.

An additional property associated with the use of steroid saponins is that they ameliorate skin irritation arising from the optional use of ultraviolet light treatment. This aspect of the surfactant ingredient is advantageous, but is not required for satisfactory results.

The third ingredient in the invention composition is a humectant-emollient. Such materials which are useful herein are those which are pharmacologically and physiologically tolerated by the distressed skin surface, which impart a favorable consistency to the compositions for their topical application to the skin and which facilitate the taking up of the composition by absorption and/or resorption and/or presorption. A suitable humectant-emollient is glycerin. Glycerin has excellent solubility in aqueous solutions, as well as the ability to provide lubricity and consistency to the composition, thus allowing an improvement in the uniformity and ease of application of the composition to the skin. Also, the humectant-emollient serves to maintain all of the components in suspension and uniformly dispersed in the carrier liquid so that the composition acts like a homogenous solution and the active ingredients are uniformly spread across the damaged area of the skin, so that the resulting peel will be uniform. Thus, while the humectant-emollient does not itself enhance the action of the acid/surfactant combination, it causes that action to be more evenly effected over the skin surface. Other humectant-emollient compounds, such as other polyhydric alcohols, polyalkylene glycols and aloe vera, may also be used as long as they are compatible with the other components of the composition.

In the compositions of the invention the humectant-emollient will be present in a concentration of about 1.0% to 20.0%.

The composition of the instant invention can also contain small amounts of antioxidants to prevent oxidative destruction of those components of the composition susceptible thereto Suitable antioxidants as well as their uses are described in "Antioxidants" in Volume 8 of Ullman's *Encyclopedia of Technical Chemistry* (4th ed., 1972). In addition, the composition may also contain small amounts of chemical preservatives to prevent or retard microbial degradation. Examples of useful preservatives are described on pages 440 to 461 in Volume 11 of Ullman's *Encyclopedia of Technical Chemistry*, (3rd ed., 1960). In general, the addition of about 0.01% to 0.2% each of preservative or antioxidant, relative to the total composition, is sufficient. also The compositions of the present invention may contain an emulsifier, generally in a concentration in the range of 0.2% to 1.0%. A number of known emulsifiers will be suitable. Particularly preferred are the $C_{10}-C_{22}$ aliphatic monocarboxylic acid salts, such as calcium, magnesium, aluminum or zinc stearate Mono- or diglycerides of the $C_{10}-C_{22}$ aliphatic monocarboxylic acid salts may also be used, but they are less preferred because they may tend to reduce the activity of trichloroacetic acid.

The balance of the composition will be a suitable sterile inert liquid carrier, most commonly water, which may be deionized.

For certain treatments, after application of the composition to the damaged area of skin, it is treated with light that has ultraviolet (and usually infrared) components. It is important to be aware that the purpose of light treatment is not to tan the skin; rather the light has a skin regenerating effect. Depending on the race of the individual, the duration of light treatment will vary. Any method for determining the sensitivity of a patient's skin to ultraviolet radiation may be used to first determine its sensitivity to a particular dose. These methods are well known to those skilled in the art, and consist of basically performing minimal erythema dose tests for different time periods of exposure to determine the proper dose to be administered to a particular patient. Generally, times on the order of minutes will be utilized regardless of race.

Prior to the application of the composition, the area to which it is applied can be cleaned with a suitable bacteriostatic agent.

A key feature of the instant invention is that it is applicable for treating skin of different races. It is particularly advantageously utilized to peel dark skin which otherwise has a tendency to produce uneven, nonuniform skin shading. The invention can also be used with great success to treat Oriental skin.

After application of the composition, with or without subsequent irradiation, a variety of washing and cleansing procedures can be employed to remove the composition. Subsequent care of the skin is minimal and generally consists of merely washing with any number of commercially available soap formulations After about three days following application, noticeable peeling will occur and this should be complete at about ten days after application. During this time, the patient can employ standard facial hygienic washing procedures; in some instances, it may be desirable to apply a topical cream containing a suitable antibiotic should it appear that there is a risk of dermal infection. A further ancillary treatment to aid the peeling process, but which is not necessary for its efficacy, is the application of a suitable benzoyl peroxide cream or retinoic acid, which promotes cell regeneration in the treated area. The latter enhances the peeling process and contributes to the overall appearance of the new skin layer. At later times during the peeling process, any of a variety of moisturizing creams can be applied to the patient's skin to reduce any redness or chapping that may appear.

As an example, as organic extract of saponin-containing plants was prepared using standard synthetic organic chemistry techniques, which yielded a steroid saponin fraction. The fraction is slightly hydroscopic and yields a clear solution at a 10% concentration in water. A 20% solution has a pH of approximately 4.5 and a density of about 375 gms/liter. The steroid saponin fraction is slightly hydroscopic, water soluble and insoluble in benzene and ether. The material was the aforesaid "Complex 272" and is approved for use by the United States government under Federal Registration No. 121.1163.

It will be apparent to those that are skilled in the art that there are a variety of substitutions that can be made to the materials described above without deviating from the intended purpose of this instant invention. Thus, it is intended that the instant invention is not to be construed as being limited to the embodiments described, but rather is only limited by the scope of the appended claims.

We claim:

1. A composition for the treatment of distressed human skin which comprises a therapeutically effective amount of an acidic component selected from the group consisting of trichloroacetic acid, resorcinol or an acid which is the therapeutic equivalent of trichloroacetic acid, a skin penetrating surfactant having cell growth stimulatory and anti-irritant properties, a humectant-emollient and a liquid carrier.

2. A composition as in claim 1 wherein said acidic component is trichloroacetic acid.

3. A composition as in claim 1 wherein said surfactant is a saponin.

4. A composition as in claim 1 wherein said saponin is a steroid saponin.

5. A composition as in claim 1 wherein said surfactant comprises a mixture of saponins.

6. A composition as in claim 5 wherein said mixture includes at least one steroid saponin.

7. A composition as in claim 1 wherein said carrier is water.

8. A composition as in claim 1 wherein said humectant-emollient is glycerin.

9. A composition as in claim 1 further comprising an emulsifier.

10. A composition as in claim 9 wherein acid emulsifier is a $C_{10}-C_{22}$ aliphatic monocarboxylic acid salt.

11. A composition as in claim 1 comprising 10% to 50% of said acidic component, 0.5% to 2.0% of said surfactant, 1.0% to 20.0% of said humectant-emollient and the balance water.

12. A composition as in claim 12 wherein said acidic component is trichloroacetic acid.

13. A composition as in claim 11 wherein said surfactant is a saponin.

14. A composition as in claim 13 wherein said saponin is a steroid saponin.

15. A composition as in claim 11 wherein said surfactant comprises a mixture of saponins.

16. A composition as in claim 15 wherein said mixture includes at least one steroid saponin.

17. A composition as in claim 16 wherein said humectant-emollient is glycerin.

18. A composition as in claim 11 further comprising 0.2% to 1.0% of an emulsifier.

19. A composition as in claim 18 wherein said emulsifier is a $C_{10}$–$C_{22}$ aliphatic monocarboxylic acid salt.

20. A composition as in claim 11 wherein said carrier is water.

21. A composition as in claim 11 further comprising 0.01% to 0.2% of an antioxidant.

22. A composition as in claim 11 further comprising 0.01% to 0.2% of a preservative.

* * * * *